(12) United States Patent
Sant et al.

(10) Patent No.: US 7,094,810 B2
(45) Date of Patent: Aug. 22, 2006

(54) PH-SENSITIVE BLOCK COPOLYMERS FOR PHARMACEUTICAL COMPOSITIONS

(75) Inventors: Vinayak Sant, Montreal (CA); Jean-Christophe Leroux, Montreal (CA)

(73) Assignee: Labopharm, Inc., Quebec (CA)

(*) Notice: Subject to any disclaimer, the term of this patent is extended or adjusted under 35 U.S.C. 154(b) by 586 days.

(21) Appl. No.: 10/607,446

(22) Filed: Jun. 25, 2003

(65) Prior Publication Data
US 2004/0072784 A1   Apr. 15, 2004

Related U.S. Application Data

(63) Continuation-in-part of application No. 09/877,999, filed on Jun. 8, 2001, now Pat. No. 6,939,564.

(51) Int. Cl.
A61K 47/30   (2006.01)
A61K 47/32   (2006.01)
A61K 47/34   (2006.01)

(52) U.S. Cl. ........ 514/772.1; 514/772; 514/772.3; 424/450; 424/489

(58) Field of Classification Search ............ None
See application file for complete search history.

(56) References Cited

U.S. PATENT DOCUMENTS

| | | | |
|---|---|---|---|
| 4,870,005 A * | 9/1989 | Akiyoshi et al. | 435/7.93 |
| 5,492,996 A * | 2/1996 | Dang et al. | 528/171 |
| 5,510,103 A | 4/1996 | Yokoyama et al. | |
| 5,620,850 A | 4/1997 | Bamdad et al. | |
| 5,656,611 A | 8/1997 | Kabanov et al. | |
| 5,693,751 A | 12/1997 | Sakurai et al. | |
| 5,702,717 A | 12/1997 | Cha et al. | |
| 5,770,627 A | 6/1998 | Inoue et al. | |
| 5,786,387 A | 7/1998 | Watanabe et al. | |
| 5,840,319 A | 11/1998 | Alakhov et al. | |
| 5,908,777 A | 6/1999 | Lee et al. | |
| 5,925,720 A | 7/1999 | Kataoka et al. | |
| 5,929,177 A | 7/1999 | Kataoka et al. | |
| 5,939,453 A | 8/1999 | Heller et al. | |
| 5,955,509 A | 9/1999 | Webber et al. | |
| 6,217,912 B1 | 4/2001 | Park et al. | |
| 6,221,959 B1 | 4/2001 | Kabanov et al. | |
| 6,372,203 B1 | 4/2002 | Allwohn et al. | |
| 6,440,743 B1 | 8/2002 | Kabanov et al. | |
| 6,491,901 B1 | 12/2002 | Gers-Barlag et al. | |
| 2002/0187199 A1 | 12/2002 | Ranger et al. | |

FOREIGN PATENT DOCUMENTS

| | | | |
|---|---|---|---|
| EP | 0 639 592 | * | 8/1993 |
| EP | 0963758 | | 12/1999 |
| GB | 141 1843 | * | 8/1975 |
| WO | WO96/21036 | | 7/1996 |
| WO | WO96/32841 | | 10/1996 |
| WO | WO97/33737 | | 9/1997 |
| WO | WO98/19710 | | 5/1998 |
| WO | WO98/37902 | | 9/1998 |
| WO | WO01/87227 | | 11/2001 |
| WO | WO2004/035013 | | 4/2004 |

OTHER PUBLICATIONS

B. Lele et al, "Mucoadhesive drug carriers based on complexes of poly(acrylic acid) and PEGylated drugs having hydrolysable PEG-anhydride-drug linkages", Journal of Controlled Release, 69:237-248 (2000).

V. Coessens et al, "Functional polymers by atom transfer radical polymerization", Prog. Polym. Sci., 26:337-377 (2001).

Y. Kakizawa et al, "Environment-sensitive stabilization of core-shell structured polyion complex micelle by reversible cross-linking of the core through disulfide bond", J. Am. Chem. Soc., 121:11247-11248 (1999).

K. Kataoka et al, "Spontaneous formation of polyion complex micelles with narrow distribution from antisense oligonucleotide and cationic block cvopolymer in physiological saline", Macromolecules, 29:8556-8557 (1996).

Scholz et al, "A novel reactive polymeric micelle with aldehyde groups on its surface", Macromolecules, 28:7295-7297 (1995).

Lee et al, "Synthesis and micellar characterization of amphiphilic diblock copolymers based on poly(2-ethyl-2-oxazoline) and aliphatic polyesters", Macromolecules, 32:1847-1852 (1999).

Benahmed et al, "Novel polymeric micelles based on the amphiphilic diblock copolymer poly(N-vinyl-2-pyrrolidone)-block-poly(D,L-lactide)", Pharmaceut. Res., 18(3):323-328 (2001).

K. Kataoka et al, "Doxorubicin-loaded poly(ethylene glycol)-poly(beta-benzyl-L-aspartate) copolymer micelles: their pharmaceutical characteristics and biological significance", Journal of Controlled Release, 64:143-153 (2000).

(Continued)

Primary Examiner—Gollamudi S. Kishore
Assistant Examiner—Eric Silverman
(74) Attorney, Agent, or Firm—McHale & Slavin, P.A.

(57) ABSTRACT

The present invention relates to a pharmaceutical composition of a biologically active agent and a block copolymer composed of a poly(ethylene oxide) forming hydrophilic segment and a poly(butyl (alkyl)acrylate-co-(alkyl)acrylic acid) that is capable of forming supramolecular assemblies or micelles under favourable conditions. The supramolecular assemblies or micelles formed from said polymers associate or dissociate reversibly upon changes in the environmental pH. The pharmaceutical compositions of the present invention contain hydrophobic drugs, cations or polycationic compounds, which can be delivered to the body by oral route or other routes of administration.

23 Claims, 2 Drawing Sheets

OTHER PUBLICATIONS

K. Kataoka et al, "Design of nanoscopic vehicles for drug targeting based on micellization of amphiphilic block copolymers", J.M.S.-Pure Appl. Chem., A31(11):1759-1769 (1994).

L. Zhang et al, "Multiple morphologies of "crew-cut" aggregates of polystyrene-b-poly(acrylic acid) block copolymers", Science, 268:1728-1731 (1995).

C. Allen et al, "Nano-engineering block copolymer aggregates for drug delivery", Colloids and Surfaces b: Biointerfaces, 16:1-24 (1999).

C-L. Zhao et al, "Fluorescence probe techniques used to study micelle formation in water-soluble block copolymers", Langmuir, 6:514-516 (1990).

A. Kabanov et al, "The neuroleptic activity of haloperidol increases after its solubilization in surfactant micelles", FEBS Letters, 258(2):343-345 (1989).

G. Kwon et al, "Polymeric micelles as new drug carriers", Advanced Drug Delivery Reviews, 21:107-116 (1996).

Inoue et al, "An AB block copolymer of oligo(methyl methacrylate) and poly(acrylic acid) for micellar delivery of hydrophobic drugs", J. Controlled Release, 51:221-229 (1998).

M. Heller et al, "Co9nformational stability of lyophilized PEGylated proteins in a phase-separating system", Journal of Pharmaceutical Sciences, 88(1):58-64 (1999).

L. Stryer, in Biochemistry, Chapter 7, pp. 154-155, fourth edition, W. H. Freeman and Company, New York (1995).

M-C. Jones et al, "Polymeric micelles-a new generation of colloidal drug carriers", European Journal of Pharmaceutics and Biopharmaceutics, 48:101-111 (1999).

S. Fullerton et al, "Molecular and population genetic analysis of allelic sequence diversity at the human beta-globin locus", Proc. Natl. Acad. Sci. USA, 91(5):1805-1809 (1994), (GenBank Accession No. AAA21101, published Aug. 6, 1994—retrieved from http://www.ncbi.nlm.nih.gov:80/entrez/viewer.fcgi?db=protein&val=532507 on Mar. 30, 2004).

S. Liebhaber et al, "Cloning and complete nucleotide sequence of human 5'-alpha-globin gene", Proc. Natl. Acad. Sci. USA, 77(12):7054-7058 (1980), (GenBank Accession No. CAA23748 published Apr. 24, 1993—retrieved from http://www.ncbi.nlm.nih.gov:80/entrez/viewer.fcgi?db=protein&val=51618 on Mar. 30, 2004).

C. Freiji-Larsson et al, "Polyurethane surfaces modified by amphiphilic polymers: effects on protein adsorption", Biomaterials, 21:307-315 (2000).

* cited by examiner

PH-SENSITIVE BLOCK COPOLYMERS FOR PHARMACEUTICAL COMPOSITIONS

REFERENCE TO RELATED APPLICATION

This application is a continuation-in-part of U.S. Ser. No. 09/877,999, filed Jun. 8, 2001 now U.S. Pat. No. 6,939,564, the contents of which is incorporated herein by reference, in its entirety.

FIELD OF THE INVENTION

The present invention relates to stimuli responsive amphiphilic polymers forming supramolecular assemblies or micelles in the nanometric size range under favourable conditions. These supramolecular assemblies or micelles can be useful for the oral or parenteral delivery of hydrophobic or cationic pharmaceutical agents.

BACKGROUND OF THE INVENTION

Amphiphilic block copolymers having optimal hydrophilic and hydrophobic segments self-assemble spontaneously in aqueous environment forming micelles or supramolecular assemblies. These supramolecular assemblies exhibit core-shell architecture wherein the hydrophobic part forms the core and the hydrophilic part forms the corona. Recently, polymeric micelles have been widely used as drug delivery carriers for parenteral administration. Micellar drug delivery carriers have several advantages including biocompatibility, solubilization of hydrophobic drugs in the core, nanometric size ranges which facilitate extravasation of the drug carrier at the site of inflammation, site-specific delivery etc. (see for example Torchilin VP, J Controlled Release, 2001, 73 137–172; Kataoka et al, Adv Drug Deliv Rev, 2001, 47, 113–131; Jones et al, Eur J Pharm Biopharm, 1999, 48, 101–111).

A large number of amphiphilic block copolymers, having nonionic and/or charged hydrophobic and hydrophilic segments, that form micelles are reported in the literature. Examples of some widely used block copolymers for parenteral delivery include poly(ethylene oxide)-b-poly(D,L-lactide), poly(ethylene oxide)-b-poly(ε-caprolactone), poly(ethylene oxide)-b-poly(aspartic acid), poly(N-vinyl pyrrolidone)-b-poly(D,L-lactide) etc.

U.S. Pat. No. 6,322,805 describes polymeric drug carrier micelles prepared from amphiphilic block copolymer having a hydrophilic poly(alkylene oxide) component and a biodegradable hydrophobic component selected from a group consisting of poly(lactic acid), poly(lactic-co-glycolic acid), poly(ε-caprolactone) and a derivative thereof. These micelles are capable of solubilizing hydrophobic drug in a hydrophilic environment.

U.S. Pat. No. 6,338,859 describes polymeric micelle compositions where the hydrophilic component includes poly(N-vinyl-2-pyrrolidone) and the hydrophobic component is selected from a group consisting of polyesters, polyorthoesters, polyanhydride and derivatives thereof. The polyester group can be selected from poly(D,L-lactic acid), poly(glycolic acid), lactide/glycolide copolymers, poly(ε-caprolactone) and derivatives thereof. The micelle composition contains a therapeutic agent which can be an antitumor compound, hydrophobic antibiotic, hydrophobic antifungal agent, an immunomodulator, an antiviral drug, or the like.

U.S. Pat. No. 6,383,811 describes formation of complexes of polyions such as DNA with polyampholytes i.e. polymers possessing both cationic and anionic moieties, and delivery of the complex into the cell.

U.S. Pat. No. 6,210,717 describes a composition composed of mixed polymeric micelles made of amphiphilic polyester-polycation copolymer and an amphiphilic polyester-sugar copolymer for delivery of nucleic acids into targeted host cells. The polyester-polycation forms an electrostatic interaction with polyanionic nucleic acids, and the polyester-sugar copolymer directs the micelle-nucleic acid complex to cells in vivo.

U.S. Pat. No. 6,429,200 describes delivery of polynucleotides to cells using cleavable reverse micelles. Other molecules such as polymers, and surfactants containing disulphide linkages can be included into the complex micelles to enhance the delivery.

U.S. Pat. No. 5,510,103 describes block copolymers having the hydrophilic and hydrophobic segments forming micelles and entrapping the hydrophobic drugs by physical methods. The hydrophilic segment is preferably poly(ethylene oxide) and hydrophobic segment is preferably poly(ε-benzyl-L-aspartate) while the preferred drug is adriamycin.

U.S. Pat. No. 5,955,509 describes use of poly(vinyl-N-heterocycle)-b-poly(alkylene oxide) copolymers in micelle containing pharmaceutical formulations. These copolymers respond to pH changes in the environment and can be used to deliver therapeutic compounds at lower pH values. The micelles of these polymers remain intact at neutral pH, e.g. at physiological pH, while they will release the contents when exposed to a lower pH environment such as in the tumor.

U.S. Pat. No. 6,497,895 describes hyperbranched micelles containing a core of mucic acid esters for the encapsulation of hydrophobic molecules. These polymers are useful for the transdermal delivery of the entrapped agent in a controlled manner.

U.S. Pat. No. 6,387,406 describes compositions of the poly(oxyethylene)-poly(oxypropylene) block copolymers for oral delivery of biological agents.

Nishiyama et al (Pharm Res 2001, 18, 1035–1041; J Controlled Release 2001, 74, 83–94) have described the use of poly(ethylene oxide)-b-poly(α,β-aspartic acid) block copolymers forming micelles by interaction with an antitumor drug, specifically cisplatin.

Though the majority of these polymers can be used for oral delivery of bioactive agents, what is presently lacking are amphiphilic polymers capable of forming supramolecular assemblies that respond to an environmental stimuli such as pH change, thereby entrapping the contents in the micelle core at a low pH, such as that prevailing in the stomach, and rapidly releasing the contents at a higher pH, such as that prevailing in the intestine.

In our earlier filed U.S. patent application (Ser. No. 09/877,999, Jun. 8, 2001) we describe a series of ionizable diblock copolymers useful for the delivery of bioactive agents. A series of the polymers in this patent application partially fulfills the above requirement. These polymers are different from those disclosed in U.S. Pat. No. 5,955,509 in that they form supramolecular assemblies at low pH, that could be dissociated upon increase in the pH above pKa of the carboxyl group. Another characteristic of these polymers is the presence of nonionizable and reversibly ionizable groups in the hydrophobic segment, where, hydrophobicity can be changed by controlling the ionization.

SUMMARY OF THE INVENTION

The present invention relates to polymers useful in combination with pharmaceutical compositions containing at least one biologically active agent. More particularly, the invention relates to block copolymers having hydrophilic and hydrophobic segments suitable for, but not limited to, oral drug delivery. More particularly, the hydrophilic segment of the polymers is nonionic and the hydrophobic segment contains at least one reversibly ionizable pendant carboxyl group conferring pH-sensitivity to the polymers.

Accordingly, it is a primary objective of the instant invention to provide a copolymer which is composed of a hydrophilic segment made of poly(ethylene oxide) and a hydrophobic segment composed of vinyl monomers containing at least one pendant carboxyl group. More particularly, the vinyl monomers included in the polymer are acrylic acid or methacrylic acid having pendant carboxyl groups and butyl (alkyl)acrylate where the butyl segment can be a linear or branched chain. Thus, the hydrophobic segment is a mixture of non-ionizable butyl (alkyl)acrylate and ionizable (alkyl)acrylic acid which controls the hydrophobicity of the polymer.

Another objective of the instant invention is to prepare pharmaceutical compositions from the instantly disclosed polymers by entrapping at least one substance, preferably a biologically active agent, which is illustrated by, albeit not limited to a hydrophobic molecule, a cationic compound or macromolecule such as peptides and proteins bearing cationic residues. The entrapment can be physical (e.g. hydrophobic interaction, electrostatic interaction), or chemical (e.g. covalent linkage) in nature.

A further objective of the present invention is to prepare supramolecular assemblies having core-shell structure wherein the core is formed by the hydrophobic segment, which can reversibly dissociate and associate in response to a change in environmental pH because of the pendant carboxyl group. The size of these supramolecular assemblies can be between 5 to 1000 nanometers thereby forming a solution or colloidal dispersion in water. It is to be noted that in the further text terms "micelles" and "supramolecular assemblies" are used interchangeably and essentially mean structures having a size range of between about 5 to 1000 nanometers.

Yet another objective of the instant invention is to describe methods of entrapping the hydrophobic agents and cationic molecules in the supramolecular assemblies giving high incorporation efficiencies.

A still further objective of the present invention is to use these supramolecular assemblies for delivery of a bioactive agent into the body by, but not limited to, the oral route. Upon oral administration, the hydrophobic molecule trapped in the core of the supramolecular assembly will be protected from the harsh acidic conditions of the stomach and released in the intestine due to dissociation of micelle at high pH.

Other objectives and advantages of this invention will become apparent from the following description, inclusive of the experimental working examples, taken in conjunction with the accompanying drawings wherein are set forth, by way of illustration and example, certain embodiments of this invention. The drawings constitute a part of this specification and include exemplary embodiments of the instant invention and illustrate various objects and features thereof.

DETAILED DESCRIPTION OF THE INVENTION

Figure 1:
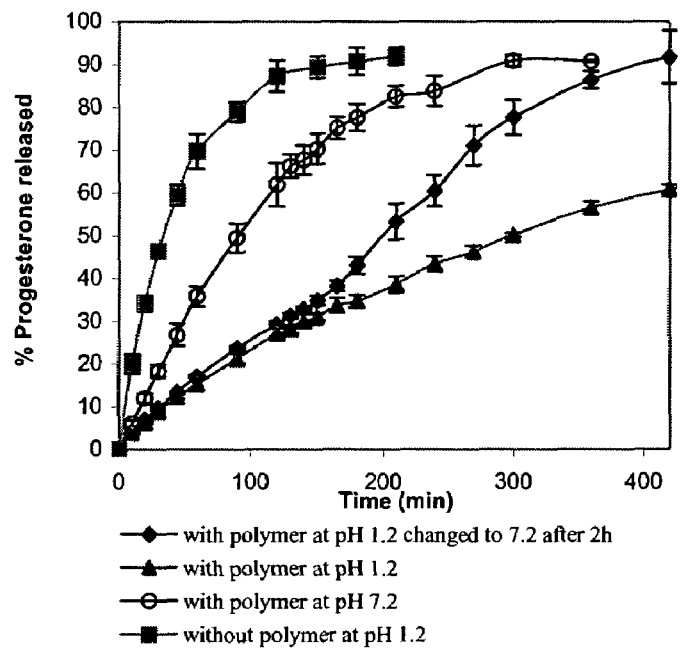
FIG. 1. demonstrates in vitro release of progesterone from PEO-b-poly($nBA_{50}$-co-$MAA_{50}$) supramolecular assemblies as a function of pH.

Abbrevations:
nBA-n-butyl acrylate;
MAA-methacrylic acid;
EA-ethyl acrylate;
PEO-poly(ethylene oxide).

The present invention describes pharmaceutical compositions composed of block polymers composed of a poly (ethylene oxide) forming the hydrophilic segment and a poly(butyl (alkyl)acrylate-co-(alkyl)acrylic acid) forming the hydrophobic segment; and at least one biologically active agent. The molecular weight of the hydrophilic segment can be in the range of 200 to 80,000 Da, more preferably in the range of 500 to 10,000 Da, still more preferably in the range of 2,000 to 5,000 Da. The hydrophobic segments of the polymers in the present invention are composed of butyl (alkyl)acrylate and (alkyl)acrylic acid, where the alkyl chain is composed of from 0 to about 10 carbon atoms, inclusively, more preferably with 0 or 1 carbon atom. The butyl segment of the butyl (alkyl)acrylate can be a linear or branched chain including without limitation n-butyl and tert-butyl groups. The mole ratio of the butyl (alkyl)acrylate: (alkyl)acrylic acid in the hydrophobic segment is in the range of about 5:95 to 95:5, more preferably in the range of about 30:70 to 70:30. The length of the hydrophobic segment can be in the range of about 200 to 50,000, more preferably in the range of about 500 to 80,000 Da.

Amphiphilic block copolymers have a tendency to self-assemble in water forming micelles. Upon micellization, the hydrophobic segment forms a core and the hydrophilic segment forms the corona of the micelles. The core of these micelles can be used as a reservoir of hydrophobic compounds protecting them form the external environment. If the hydrophobic segment of the polymer contains reversibly ionizable moieties, then the hydrophobicity of the segment could be manipulated by controlling the ionization of the moiety. Polymers of the present invention differ from other block copolymers in this aspect. In the polymers of the present invention, the hydrophobic segment is composed of the mixture of two monomers, one of them is butyl (alkyl) acrylate, which confers hydrophobicity to the segment. Butyl (alkyl)acrylate monomer is more preferably butyl acrylate or butyl methacrylate. The other monomer, (alkyl) acrylic acid has a pendant carboxyl group that can be reversibly ionized by changing the environmental pH. Thus, when the environmental pH is below the pKa of the carboxyl group, it will remain mostly in the unionized form and will confer hydrophobicity to the segment. This results in spontaneous aggregation of polymeric chains forming stable supramolecular assemblies or micelles in aqueous environment. However, when environmental pH is increased above pKa of the carboxyl group, its ionization will impart hydrophilicity to the hydrophobic segment. This may result in the dissociation of the micelle. (Alkyl)acrylic acid monomer is more preferably acrylic acid or methacrylic acid.

These supramolecular assemblies are in the size range of from about 5 to 1000 nanometers. Hydrophobic drugs are incorporated in the core of such supramolecular assemblies by methods that are known to one of ordinary skill in the art (see for example Lavasanifar et al J Controlled Release 2001, 77,155–60; Kohori et J Controlled Release 2002,78, 155–63). Manipulation of the composition of the hydrophobic segment results in variation in the hydrophobicity of the polymer allowing control of the incorporation efficiencies of the hydrophobic drugs. Loadings in the range of 0.1 to 50% w/w more preferably in the range of 1 to 20% w/w of hydrophobic drugs are obtained using different drug loading procedures.

Block copolymers of the present invention are used to prepare pharmaceutical compositions containing hydrophobic molecules. Non-limiting examples of the hydrophobic molecules includes hypolipidemic agents such as fenofibrate, anticancer agents such as doxorubicin, paclitaxel, docetaxel, camptothecin, megestrol acetate, teniposide, etoposide, antihypertensive agents such as candesartan cilexetil, non-steroidal anti-inflammatory agents such as indomethacin, celecoxib, antiviral agents such as retinovir, amprenavir, indinavir, efavirenz, immunosuppressive agents such as cyclosporin A, sirolimus, tacrolimus, and similar agents belonging to other therapeutic classes.

In an alternative embodiment of the present invention, the poly(butyl (alkyl)acrylate-co-(alkyl)acrylic acid) segment of the polymer will bear a negative charge at a pH above the pKa of carboxyl groups and form complexes with cationic molecules including without limitation polycations, peptides and proteins bearing cationic residues by electrostatic interactions. This will result in the partial or complete charge neutralization of polymer and/or cationic molecule thereby forming supramolecular assemblies or micelles. The cation or polycationic molecule will be entrapped in the core of such supramolecular assemblies. The term "cationic residues" refers to the functional groups imparting positive charge to the molecule such as cationic amino acids e.g. lysine, arginine, histidine or other functional groups such as primary, secondary, tertiary or quaternary amine groups present in the molecule.

The complexes of poly(ethylene oxide)-block-poly(n-butyl acrylate-co-methacrylic acid) with poly-l-lysine are prepared in a buffer solution at pH 7.4. Supramolecular assemblies having unimodal size distribution within the size range of about 20 to 50 nm are obtained depending upon the molecular weight of the poly-l-lysine and composition of the polymer. On the other hand, complexes of poly(ethylene oxide)-block-poly(ethyl acrylate-co-methacrylic acid) with poly-l-lysine in pH 7.4 buffer results in formation of aggregates having multimodal size distribution with sizes above about 200 nm.

In yet another embodiment of the present invention, block copolymers are used to form stable coordination complexes with biologically active agents illustrated as metallic compounds such as cisplatin, carboplatin above the pKa of the carboxyl groups.

The presence of butyl (alkyl)acrylate in the hydrophobic segment plays several crucial roles in forming stable supramolecular assemblies. It confers hydrophobicity to the polymer chain, which is one of the important driving forces in the self-assembly of polymeric chains. It also increases the incorporation of hydrophobic drugs in the supramolecular assemblies. It is well known that carboxylic acid groups form intra- and/or intermolecular hydrogen-bonding complexes with oxygen present in the polyethylene oxide chain (see for example Donini et al, Int J Pharm, 2002, 245, 83–91; Lele et al, J. Controlled Release, 2000, 69, 237–248). This results in the formation of large aggregates or sometimes in precipitation of the complex. This problem could be possible in poly(ethylene oxide)-block-poly(aspartic acid) polymers (Nishiyama et al Pharm Res 2001, 18, 1035–1041; Yokoyama et al J Controlled release 1996, 39, 351–356). It was evident in polymers having the composition poly(ethylene oxide)-block-poly(methacrylic acid) as reported previously (Ranger et al J Polymer Science: part A: Polymer Chemistry, 2001, 39, 3861–3874). One method for overcoming this problem is by incorporating hydrophobic monomers such as ethyl acrylate in the hydrophobic segment, as disclosed in our earlier U.S. patent application (Ser. No. 09/877,999 Jun. 8, 2001).

In accordance with the instantly disclosed invention, it was observed that polymers with improved characteristics could be obtained by incorporating butyl (alkyl)acrylate in the hydrophobic segment. One of the major advantages of polymers in accordance with the present invention is the presence of the butyl chain of the butyl (alkyl)acrylate that largely minimizes formation of such hydrogen bonding complexes and can prevent formation of aggregates. This aids in the formation of stable supramolecular assemblies having uniform size range.

For example, poly(ethylene oxide)-block-poly(n-butyl acrylate-co-methacrylic acid) with 50:50 mole ratio of n-butyl acrylate:methacrylic acid having molecular weight of about 5300 Da forms micelles of 30 nm at pH 5.0 while poly(ethylene oxide)-block-poly(ethyl acrylate-co-methacrylic acid) with 50:50 mole ratio of ethyl acrylate: methacrylic acid having molecular weight of about 5100 Da forms micelles of 120 nm at pH 5.0, which are possibly aggregates of several micelles.

An oral route is the most preferred route of administration for a pharmaceutically active agent. For oral delivery, the compositions can be used in the form of tablets, capsules, powders, lozenges, solutions, suspensions, syrups, elixirs, and the like. The pharmaceutical compositions of the present invention are administered orally. The pharmaceutical compositions of the present invention can also be administered by a number of other routes, including without limitation, rectally, vaginally, topically, by pulmonary route, parenterally, including but not limited to intravenous, intra-arterial, intramuscular, intraperitoneal or subcutaneous route.

The polymers in the present invention can be modified to attach targeting ligands such as lectin, antibodies or fragments of antibodies, peptides, vitamins or sugar molecules.

EXAMPLES

In all further text, figures appearing as subscript in the polymer composition indicate the mole ratio of that monomer present in the hydrophobic segment of the polymer.

Example 1

In Vitro Release of $^3$H-progesterone from PEO-b-poly (nBA$_{50}$-co-MAA$_{50}$) Supramolecular Assemblies at Different pH:

Progesterone was used as a model hydrophobic drug to evaluate the effect of pH on drug release from supramolecular assemblies. $^3$H-progesterone was loaded in the supramolecular assemblies of PEO-b-poly(nBA$_{50}$-co-MAA$_{50}$) of molecular weight 5300 Da by film casting method. Briefly, 10 mg polymer, 1 mg progesterone and 1 µCi $^3$H-progesterone were dissolved in a mixture of dichloromethane, ethanol and water in a scintillation vial. The solvents were evaporated under reduced pressure to cast a film of polymer and drug on the glass surface. The film was hydrated with water to obtain the supramolecular assemblies, this solution was filtered through 2 µm filter to remove precipitated drug.

For in vitro release study, the solution of progesterone loaded supramolecular assemblies was filled in a dialysis bag (6000–8000 Da molecular weight cut off) and the bag was put in a beaker containing 200 mL of simulated gastric fluid, pH 1.2 maintained at 37° C. The release medium was magnetically stirred. After 2 hours, the pH of medium was adjusted to 7.2 by addition of sodium hydroxide and potassium dihydrogen phosphate. During the entire release experiment, 1 mL samples of release medium were withdrawn periodically to measure the radioactivity of $^3$H-progesterone. As a control, the release of $^3$H-progesterone from supramolecular assemblies was also measured at pH 1.2, pH 7.2 and at pH 1.2 in absence of polymer. The results of the release experiment are shown in FIG. 1.

As shown in FIG. 1, the progesterone is released rapidly in the absence of polymer at pH 1.2, suggesting that the dialysis bag does not form a barrier for the drug release. Further, the progesterone release from PEO-b-poly(nBA$_{50}$-co-MAA$_{50}$) supramolecular assemblies is very rapid at pH 7.2, while slow at pH 1.2. On the other hand, when the pH of the release medium is changed from 1.2 to 7.2 after 2 hours, the release rate increases significantly. This is evidentiary of pH dependent dissociation of supramolecular assemblies. At pH 1.2, the polymer exists in the form of supramolecular assemblies due to unionized carboxyl groups and the drug is released slowly from the core of supramolecular assemblies. However, when the pH is increased to 7.2, the carboxyl groups become ionized resulting in the dissociation of supramolecular assemblies and the drug is released rapidly.

Figure 2:
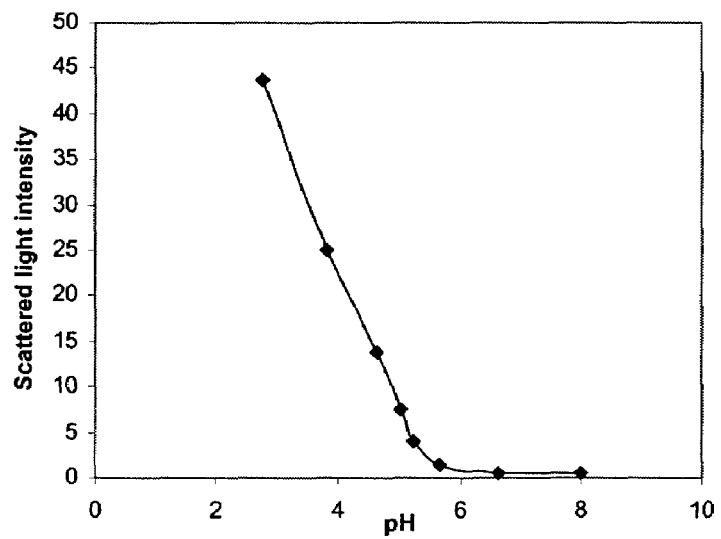
FIG. 2: demonstrates the effect of pH on intensity of light scattered by solution of PEO-b-poly($nBA_{50}$-co-$MAA_{50}$)

To support this data, pH dependent aggregation behavior of PEO-b-poly(nBA$_{50}$-co-MAA$_{50}$) was studied using dynamic light scattering. Polymer solutions (0.5 mg/mL) were prepared in citrate phosphate universal buffer and the pH was adjusted between about 2.2–7.0. The intensity of scattered light from these solutions at different pH was measured at 25° C. and 90° angle and was plotted as a function of pH. The results are shown in FIG. 2.

From FIG. 2, it is evident that the scattered light intensity is negligible at pH above ~5.5 while when the pH is decreased below 5.5, the intensity increases significantly suggesting association of polymeric chains. This indicates that below pH 5.5 the polymer is present in the form of supramolecular assemblies. The size of these supramolecular assemblies is in the range of 30–100 nm depending upon the environmental pH.

Example 2

Bioavailability Studies of Fenofibrate Entrapped in Supramolecular Assemblies upon Oral Administration to Rats Fenofibrate (FNB) was used as a model poorly water-soluble hydrophobic drug to evaluate the effect of drug incorporation in supramolecular assemblies on the bioavailability upon oral administration to rats. In a series of experiments, FNB incorporation was studied in different PEO-b-poly(EA-co-MAA) and PEO-b-poly(nBA$_{50}$-co-MAA$_{50}$) polymers by emulsion and film casting methods. The FNB loading was higher in PEO-b-poly(nBA$_{50}$-co-MAA$_{50}$) polymers. Therefore these polymers were used to evaluate relative bioavailability of FNB loaded supramolecular assemblies in Sprague-Dawley rats.

The study was conducted on 3 fenofibrate formulations, namely FNB supramolecular assemblies, FNB standard formulation and resuspended FNB. FNB loaded supramolecular assemblies were prepared from PEO-b-poly(nBA$_{50}$-co-MAA$_{50}$) of about molecular weight 5300 Da by film casting method. Size of the supramolecular assemblies was in the range of about 100–300 nm. FNB standard formulation was prepared by suspending the powder from Lipidil Macro® (Fournier) capsule in 0.5% w/v carboxymethyl cellulose sodium (CMC Na) solution to obtain uniform suspension. FNB powder (Sigma) was also suspended in 0.5% w/v CMC Na solution to prepare resuspended FNB formulation which acts as a negative control.

Figure 3:
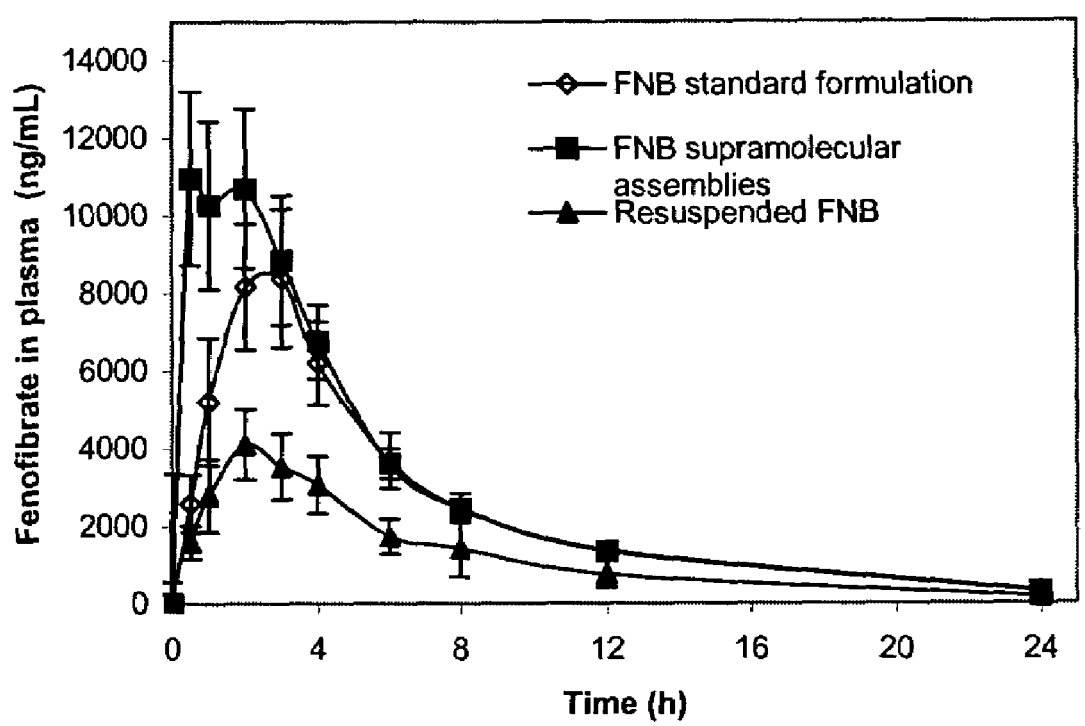
FIG. 3. is a plot of plasma concentration versus time of fenofibrate upon oral administration of different formulations to Sprague-Dawley rats.

Rats were divided into 3 groups of 6 animals each. The rats were fasted overnight and fed with standard diet throughout the study. Each formulation was administered orally at a dose of 7.5 mg/kg to 6 rats from a group. Blood was removed periodically from each rat, plasma was separated and stored at −80° C. till further use. FNB content from the plasma was determined and plotted against time, the results of which are shown in FIG. 3.

The results show that FNB incorporated in supramolecular assemblies results in highest peak plasma level, ie. 10.9 µg/mL compared to 8.4 µg/mL for standard formulation. Also, $t_{max}$ was achieved rapidly by FNB loaded supramolecular assemblies compared to standard formulation. Overall, the relative bioavailability of FNB was enhanced by 19% upon entrapment in supramolecular assemblies compared to standard FNB formulation, and the bioavailability enhancement was 133% compared to resuspended FNB powder. This enhancement in relative bioavailability is possibly due to release of drug from supramolecular assemblies in the nanoscopic size range, which increases the rate of dissolution of drug.

Example 3

Formation of Polyion Complex Micelles of PEO-b-P(nBA$_{50}$-co-MAA$_{50}$) with poly-l-lysin Poly-l-lysine (PLL) of molecular weight 16,100 was used as a model cationic compound for formation of polyion micelles with PEO-b-P(EA$_{50}$-co-MAA$_{50}$) and PEO-b-P(nBA$_{50}$-co-MAA$_{50}$) copolymers with molecular weights of 5100 and 5700 Da, respectively. Polymer: PLL (−/+) charge ratios (mole: mole) of 1:1 and 2:1 were used for complex formation. Stock solutions of polymer and PLL (molecular weight 16,100) having concentration of 2.5 mg/mL were prepared in phosphate buffer (pH 7.4) and mixed at room temperature to obtain 1 mg/mL final polymer concentration. The solution was filtered through 0.2 µm filter and size measurements were performed at 25° C. using dynamic light scattering (DLS). The results are shown in Table 1.

TABLE 1

Size of different polymer: PLL polyion micelles

| Polymer | Charge ratio (mol/mol) | Diameter (nm) mean ± SD | % Population | Polydispersity Mean ± SD |
|---|---|---|---|---|
| PEO-b-P(EA$_{50}$-co-MAA$_{50}$) | 1:1 | 1049 ± 170<br>35 ± 3.2 | 65<br>35 | 0.571 ± 0.199 |
| PEO-b-P(EA$_{50}$-co-MAA$_{50}$) | 2:1 | 220 ± 5.1 | 100 | 0.448 ± 0.024 |

TABLE 1-continued

Size of different polymer: PLL polyion micelles

| Polymer | Charge ratio (mol/mol) | Diameter (nm) mean ± SD | % Population | Polydispersity Mean ± SD |
|---|---|---|---|---|
| PEO-b-P(nBA$_{50}$-co-MAA$_{50}$) | 1:1 | 31 ± .028 | 100 | 0.058 ± 0.012 |
| PEO-b-P(nBA$_{50}$-co-MAA$_{50}$) | 2:1 | 32 ± 0.2 | 100 | 0.11 ± 0.019 |

The results of Table 1 show that complexation of PLL with PEO-b-P(EA$_{50}$-co-MAA$_{50}$) at different charge ratios results in formation of relatively large aggregates which could be attributed to the hydrogen bonding between poly(ethylene oxide) chain and carboxyl groups. In contrast, the complexation of PLL with PEO-b-P(nBA$_{50}$-co-MAA$_{50}$) at similar ratios results in formation of micelles having unimodal size distribution and low polydispersity indices. Similar complexes are obtained with PLL of different molecular weights.

Example 4

Complexation of PEO-b-P(nBA$_{50}$-co-MAA$_{50}$) with Verapamil Hydrochloride

Verapamil hydrochloride was used as a model cationic drug. Solutions of PEO-b-P(nBA$_{50}$-co-MAA$_{50}$) and verapamil hydrochloride in universal buffer were mixed to obtain final polymer concentration of 0.5 mg/mL and verapamil hydrochloride concentration of 0.8 mg/mL. The solution pH was adjusted to 6.1 and size was measured using DLS. Polyion complex micelles of 38±10.3 nm were obtained.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

One skilled in the art will readily appreciate that the present invention is well adapted to carry out the objects and obtain the ends and advantages mentioned, as well as those inherent therein. The compounds, compositions, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims.

Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A pharmaceutical composition comprising:
   a diblock copolymer of poly(ethylene oxide) and poly (butyl (alkyl)acrylate-co-(alkyl)acrylic acid); and at least one biologically active agent.

2. The polymer of claim 1 wherein said poly(ethylene oxide) segment has a molecular weight in the range of about 200–80,000 Da.

3. The polymer of claim 1 wherein said poly(butyl (alkyl) acrylate-co-(alkyl)acrylic acid) segment has a molecular weight in the range of about 200–80,000 Da.

4. The polymer of claim 1 wherein said alkyl is an alkyl chain having from 0 to about 10 carbon atoms.

5. The polymer of claim 1 wherein said butyl portion of the butyl (alkyl)acrylate is a linear or branched chain.

6. The polymer of claim 1 wherein said butyl (alkyl) acrylate:(alkyl)acrylic acid is in a molar ratio in the range of about 5:95 to 95:5.

7. The pharmaceutical composition of claim 1 wherein said diblock polymer is poly(ethylene oxide)-block-poly(n-butyl acrylate-co-methacrylic acid) having an n-butyl acrylate:methacrylic acid molar ratio of about 50:50.

8. The pharmaceutical composition of claim 1 in the form of supramolecular assemblies or micelles.

9. The pharmaceutical composition of claim 8 wherein said supramolecular assemblies or micelles are in a size range of about 5 to 1000 nanometers.

10. The pharmaceutical composition of claim 8 wherein said supramolecular assemblies associate or dissociate reversibly in response to environmental pH changes.

11. The pharmaceutical composition of claim 1 wherein release rate of said biologically active agent increases with increase in pH.

12. The pharmaceutical composition of claim 8 wherein the biologically active agent is a hydrophobic drug incorporated in said supramolecular assemblies by physical or chemical methods.

13. The pharmaceutical composition of claim 12 wherein the hydrophobic drug is fenofibrate.

14. The pharmaceutical composition of claim 8 wherein the biologically active agent is a cation or polycation.

15. The pharmaceutical composition of claim 14 wherein said polycation is a peptide or protein bearing cationic residues.

16. The pharmaceutical composition of claim 14 wherein the cation or polycation interacts electrostatically with said (alkyl)acrylic acid units.

17. The pharmaceutical composition of claim 14 wherein the cation is verapamil hydrochloride.

18. The pharmaceutical composition of claim 8 wherein the biologically active agent forms metal coordination complexes with said (alkyl)acrylic acid units.

19. The pharmaceutical composition of claim 18 wherein the biologically active agent is cisplatin.

20. The pharmaceutical composition of claim 18 wherein the biologically active agent is carboplatin.

21. The pharmaceutical composition of claim 12 wherein incorporation of a hydrophobic drug in the supramolecular assemblies enhances the bioavailability of the hydrophobic drug upon oral administration.

22. The pharmaceutical composition of claim 8 which is administered by oral, intravenous, intra-arterial, subcutaneous, intramuscular, intraperitoneal, rectal, vaginal or topical route.

23. The pharmaceutical composition of claim 8 having a targeting ligand on a surface thereof.

* * * * *